United States Patent
Komatsu et al.

(10) Patent No.: US 6,476,258 B1
(45) Date of Patent: Nov. 5, 2002

(54) PROCESS FOR PRODUCING ARYLOXYACETIC ACIDS

(75) Inventors: Masashi Komatsu, Nishinomiya (JP); Junichi Ishikawa, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/609,928

(22) Filed: Jul. 5, 2000

(30) Foreign Application Priority Data

Jul. 7, 1999 (JP) .......................................... 11-193360
Jul. 12, 1999 (JP) .......................................... 11-197241

(51) Int. Cl.$^7$ ......................... C07C 51/16; C07C 61/12; C07C 62/00
(52) U.S. Cl. ..................... 562/421; 562/499; 562/508; 562/537; 562/538
(58) Field of Search ............................... 562/308, 421, 562/499, 537, 538

(56) References Cited

U.S. PATENT DOCUMENTS

| | | | |
|---|---|---|---|
| 3,855,307 A | * | 12/1974 | Rony et al. |
| 4,238,625 A | * | 12/1980 | Fiege et al .................. 62/421 |
| 4,306,083 A | * | 12/1981 | Ma |
| 4,804,777 A | | 2/1989 | Sumner, Jr. et al. |
| 4,935,540 A | | 6/1990 | Sumner, Jr. et al. |
| 4,976,893 A | * | 12/1990 | Leupold |

FOREIGN PATENT DOCUMENTS

| | | | |
|---|---|---|---|
| JP | 54-138886 | | 10/1979 |
| JP | 54138886 | * | 10/1979 |
| JP | 3-38544 | | 2/1991 |
| JP | 6-40960 B2 | * | 6/1994 |
| JP | 6-40961 B2 | * | 6/1994 |

* cited by examiner

Primary Examiner—Alan L. Rotman
Assistant Examiner—Hector M Reyes
(74) Attorney, Agent, or Firm—Sughrue Mion, PLLC

(57) ABSTRACT

An industrially advantageous process for producing an aryloxyacetic acid represented by the formula (2):

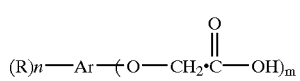

(2)

wherein m represents an integer of 1 or 2, n represents an integer from 0 to 4, Ar represents a aromatic hydrocarbon ring, each Rs independently represents an alkyl group, a cycloalkyl group, an aryl group, an alkoxy group, a cycloalkoxy group, an aryloxy group, a halogen atom, an alkylcarbonyl group, an arylcarbonyl group, a carboxyl group or a nitro group, comprising a step in which an oxygen-containing gas is made act on an aryloxyethanol represented by the formula (1):

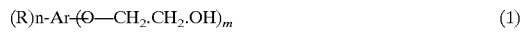

(1)

wherein m, n, Ar, and R, respectively, have the same meanings as defined above, under conditions of using a catalyst comprising palladium and an indium compound and/or a copper compound in an aqueous medium and in the presence of 0.5 m or more equivalent of alkali per one mole of the aryloxyethanol represented by the formula (1); or under conditions of using a platinum catalyst, in an aqueous medium and in the absence of alkali or in the presence of less than 0.5 m equivalent of alkali per one mole of the aryloxyethanol represented by the formula (1).

18 Claims, No Drawings

PROCESS FOR PRODUCING ARYLOXYACETIC ACIDS

BACKGROUND OF THE INVENTION

The present invention relates to a process for producing anaryloxyacetic acid, particularly to a process for producing an aryloxyacetic acid wherein an oxygen-containing gas is made act on an aryloxyethanol in an aqueous medium using a specific catalyst.

A process in which an oxygen-containing gas is made act on an aryloxyethanol by using a platinum-based catalyst in an alkali aqueous medium has been known as a process for producing an aryloxyacetic acid. For example, there have been known a process which uses platinum, or palladium and bismuth, or lead as a catalyst (JP-A-62-28940), a process which uses palladium and silver as a catalyst (JP-A-3-500653), and a process which uses palladium and antimony or tellurium as a catalyst (JP-A-3-38544).

However, these catalysts have a problem that catalyst components were eluted into the reaction mass after completion of the reactions. This problem has hindered recycling of the catalyst.

The present inventors have conducted extensive study to find a catalyst whose components are suppressed to be eluted into a reaction mass, and have found that catalysts comprising a combination of palladium and an indium compound and/or a copper compound are excellent in anti-elution property.

In known process for producing aryloxyacetic acid, the production is carried out in the presence of one or more equivalence ratio of alkali based on the raw material, aryloxyethanol. The present inventors have also conducted extensive study on a process which is carried out in the practical absence of alkali, and have found that among platinum-based catalysts, only catalysts containing platinum as a main component can exhibit an effect as an oxidation catalyst even in the practical absence of alkali.

The present inventors have made further investigation and have accomplished the present invention.

SUMMARY OF THE INVENTION

The present invention provides an industrially advantageous process for producing an aryloxyacetic acid represented by the formula (2):

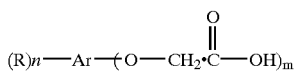

(2)

wherein m represents an integer of 1 or 2, n represents an integer from 0 to 4. Ar represents an aromatic hydrocarbon ring, each Rs independently represents an alkyl group, a cycloalkyl group, an aryl group, an alkoxy group, a cycloalkoxy group, an aryloxy group, a halogen atom, an alkylcarbonyl group, an arylcarbonyl group, a carboxyl group or a nitro group,
comprising a step in which an oxygen-containing gas is made act on an aryloxyethanol represented by the formula (1):

(1)

wherein m, n, Ar and R, respectively, have the same meanings as defined above, under conditions of using a catalyst comprising palladium and an indium compound and/or a copper compound in an aqueous medium and in the presence of 0.5 m or more equivalent of alkali per one mole of the aryloxyethanol represented by the formula (1); or under conditions of using a platinum catalyst, in an aqueous medium and in the absence of alkali or in the presence of less than 0.5 m equivalent of alkali per one mole of the aryloxyethanol represented by the formula (1).

PREFERRED EMBODIMENTS OF THE INVENTION

The present invention uses an aryloxyethanol represented by the above general formula (1) as a raw material In the formula, Ar represents an aromatic hydrocarbon ring. Examples of the aromatic hydrocarbon ring include benzene ring or naphthalene ring. When Ar is a benzene ring, the aryloxyethanol of formula (1) is represented by the general formula (1-1):

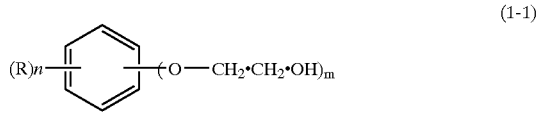

(1-1)

wherein m, n, and R, respectively, have the same meanings as defined above.

In these formulae, each Rs independently represent an alkyl group, a cycloalkyl group, an aryl group, an alkoxy group, a cycloalkoxy group, an aryloxy group, a halogen atom, an alkylcarbonyl group, an arylcarbonyl group, a carboxyl group or a nitro group.

Examples of the alkyl group as R include linear or branched hydrocarbon groups having from 1 to 12 carbon atoms such as methyl, ethyl, propyl, isopropyl, butyl, isobutyl, sec-butyl, t-butyl, pentyl, isopentyl, t-amyl, hexyl, isohexyl, heptyl, isoheptyl, t-octyl, isooctyl, nonyl, isononyl, decyl, ilsodecyl, undecyl, isoundecyl, dodecyl and isododecyl. Among them, linear or branched hydrocarbon groups having from 1 to 6 carbon atoms are preferred.

Examples of the cycloalkyl group include cyclic hydrocarbon groups having from 5 to 9 carbon atoms such as cyclopentyl and cyclohexyl Examples of the aryl group include phenyl and naphthyl. Examples of the alkoxy group include alkoxy groups having an alkyl moiety with from about 1 to about 12 carbon atoms, such as methoxy, ethoxy, propoxy, butoxy, isobutoxy, t-butoxy, pentoxy, isopentoxy, hexoxy and isohexoxy. Examples of the cycloalkoxy group include cyclopentoxy and cyclohexoxy Examples of the aryloxy group include phenoxy and naphthoxy.

The halogen atom includes fluorine, chlorine, bromine, iodine and the like, and preferred are chlorine and bromine. Preferred alkylcarbonyl groups are lower alkylcarbonyl groups having from 1 to 6 carbon atoms such as an acetyl group. Examples of the arylcarbonyl group include a benzoyl group.

Representative examples of the ayloxyethanol include 2-phenoxyethanol, 2-(2-methylphenoxy)ethanol, 2-(3-methylphenoxy)ethanol, 2-(4-methylphenoxy)ethanol, 2-(2-ethylphenoxy)ethanol, 2-(3-ethylphenoxy)ethanol, 2-(4-ethylphenoxy)ethanol, 2-(2-propylphenoxy)ethanol, 2-(3-propylphenoxy)ethanol, 2-(4-propylphenoxy)ethanol, 2-(2-isopropylphenoxy)ethanol, 2-(3-isopropylphenoxy)ethanol, 2-(4-isopropylphenoxy)ethanol, 2-(2-cyclopentylphenoxy) ethanol, 2-(3-cyclopentylphenoxy)ethanol, 2-(4- cyclopentylphenoxy)ethanol, 2-(2-cyclohexylphenoxy) ethanol, 2-(3-cyclohexylphenoxy)ethanol, 2-(4-cyclohexylphenoxy)ethanol, 2-(biphenyl-2-yloxy)ethanol, 2-(biphenyl-3-yloxy)ethanol, 2-(biphenyl-4-yloxy)ethanol, 2-(2-naphthalene-1-ylphenoxy)ethanol, 2-(3-naphthalene-1-ylphenoxy)ethanol, 2-(3-naphthalene-1-ylphenoxy)ethanol, 2-(2-naphthalene-2-ylphenoxy)ethanol, 2-(3-naphthalene-2-ylphenoxy)ethanol, 2-(4-naphthalene-2-ylphenoxy)ethanol, 2-(2-chlorophenoxy)ethanol, 2-(3-chlorophenoxy)ethanol, 2-(4-chlorophenoxy)ethanol, 2-(2-bromophenoxy)ethanol, 2-(3-bromophenoxy)ethanol, 2-(4-bromophenoxy)ethanol, 2-(2-acetylphenoxy)ethanol, 2-(3-acetylphenoxy)ethanol, 2-(4-acetylphenoxy)ethanol, 2-(2-benzoylphenoxy)ethanol, 2-(3-benzoylphenoxy)ethanol, 2-(4-benzoylphenoxy) ethanol, 2-(naphtalene-1-yloxy)ethanol, 2-(naphtalene-2-yloxy)ethanol, 1,2-bis(hydroxyethoxy)benzene, 1,3-bis(hydroxyethoxy)benzene, and 1,4-bis(hydroxyethoxy)benzene Among them, phenoxyethanol, 1,2-bis(hydroxyethoxy)benzene, 1,3-bis(hydroxyethoxy)benzene, and 1,4-bis(hydroxyethoxy)benzene and the like are preferable. Particularly preferred is 1,3-bis(hydroxyethoxy)benzene.

The present Invention provides a process in which an oxygen-containing gas is made act on the above-mentioned aryloxyethanol represented by the formula (1)

under conditions of using a catalyst comprising palladium and an indium compound and/or a copper compound (hereinafter, abbreviated by "Pd/In,Cu catalyst") in an aqueous medium and in the presence of 0.5 m or more equivalent of alkali per one mole of the aryloxyethanol represented by the formula (1); or under conditions of using a platinum catalyst (hereinafter, abbreviated by "Pt catalysts"), in an aqueous medium, and in the absence of alkali or in the presence of less than 0.5 m equivalent of alkali per one mole of the aryloxyethanol represented by the formula (1).

In the present invention, when the oxygen-containing gas is made act in an aqueous medium and in the presence of 0.5 m or more equivalent of alkali per one mole of the aryloxyethanol represented by the formula (1), a catalyst comprising palladium as a first component and a copper compound and/or an indium compound as a second component is used. An atomic ratio of the second component to palladium is generally from about 0.01 to about 20, preferably from about 0.1 to about 10.

The palladium useful in the catalyst of this invention can be in a variety of forms. Elemental palladium metal can be used. Other palladium compounds, such as the oxides, can also be used.

The copper and/or indium as the catalyst in this invention can be in a variety of forms and oxidation states. Examples of copper compounds which can be used include elemental copper metal, copper(I) salts, such as copper(I) oxide, and copper(II) salts. Examples of indium compounds which can be used are elemental indium, indium(I) salts, and indium (III) salts. By adding an indium compound and/or a copper compound to palladium, elution of palladium, indium and copper into the reaction solvent is suppressed.

In this case, a mixture of a first component and a second component or a compound thereof, composite oxides of these metals, materials obtained by coprecipitating these metals, and the like can be used as it is as a catalyst. Nevertheless, the catalyst are generally used with being supported on a carrier. Examples of the carrier include active carbon, silica gel, alumina, titania, zirconia, celite and diatom earth. Preferred is active carbon. Amount of the palladium supported on the carrier is from about 0.01 to about 30% by weight, preferably from about 0.1 to about 15% by weight relative to the weight of the carrier.

A method for making the carrier support the catalyst components thereon is not particularly limited. In general, a semi-arid supporting method, a precipitation supporting method, an equilibrium adsorption method, an ion adsorption method, an evaporation-to-dryness method, a spraying method and the like can be adopted. The catalyst components may be supported either at one time or sequentially. Further, activation may be carried out by kneading, baking or reduction, as needed. In the sequential supporting method, kneading, baking or reduction can be conducted either after supporting the first component and before supporting another component, or after supporting the first component and another component.

Amount of the catalyst to be used relative to the aryloxyethanol, the raw material, can be varied widely. Although it depends on a desired reaction rate, it is generally from 0.0001 to 1 atom, preferably from 0.005 to 0.5 atom, in terms of palladium, relative to 1 mol of the aryloxyethanol, for example, in the case of a slurry bed.

In the present invention, when the oxygen-containing gas is made act in an aqueous medium and In the absence of alkali or in the presence of less than 0.5 m equivalent of alkali per one mole of the aryloxyethanol represented by the formula (1), Pt catalyst is used. As the Pt catalyst, platinum, platinum oxide and platinum partially oxidized such as an Adams catalyst can be used. Generally, those supported on a carrier are used. Amount of the platinum supported on the carrier is usually from 0.1 to 25% by weight, preferably from 0.5 to 10% by weight. Examples of the carrier include activated carbon such as peat, charcoal, coconut shell coal and animal charcoal, activated clay, titania, zirconia, alumina and zeolite. Among them, those supported on an activated carbon, particularly peat, are preferably used. The Pt catalyst can contain metals other than platinum as a promoter. Example of the metals other than platinum include bismuth, antimony, germanium, tin, lead, gallium, indlum, thalliumandtellurium. Among them, bismuth, tellurium, lead and the like are preferred, and bismuth is particularly preferred. An amount of the metal other than platinum on the carrier is usually from 0.1 to 30% by weight, preferably from 0.5 to 20% by weight based on the total amount of catalyst.

When the catalyst contains platinum and bismuth, it is preferable that the catalyst also contain one or more metals such as chromium, molybdenum, tungsten, vanadium, niobium, tantalum, germanium, tin and lead. Amount of the metal other than platinum and bismuth on the carrier is usually from 0.1 to 30% by weight, preferably from 0.5 to 20% by weight based on the total amount of catalyst.

Amount, relative to the aryloxyethanol, of the Pt catalyst to be used can be varied widely. Although it depends on a desired reaction rate, it is generally from 0.001 to 0.1 atom, preferably from 0.005 to 0.05 atom, in terms of platinum, relative to 1 mol of the aryloxyethanol, for example, in the case of a slurry bed.

In the present invention, the oxygen-containing gas is made act on an alkyloxyethanol of formula (1) in an aqueous medium. Examples of the aqueous medium include water and mixed solvents consisting of water and a lower carboxylic acid, such as aqueous acetic acid and aqueous propionic acid. Among them, water is preferably used. The aqueous medium can also contain a surfactant inert to the reaction, an organic solvent, and the like.

Amount, by weight, of the aqueous medium to be used is generally from about 1 to about 30 times, preferably from about 5 to about 15 times, based on the amount of the aryloxyethanol.

In the present invention, when Pd/In,Cu catalyst is used, amount of the alkaline substance to be used is usually from about 0.5 m to about 30 m equivalents, preferably from about 0.8 m to about 10 m equivalents per one mole of the aryloxyethanol represented by the formula (1), wherein m has the same meaning as defined in the formula (1).

Examples of the alkaline substance include alkali metal hydroxides such as sodium hydroxide, potassium hydroxide, lithium hydroxide, alkali earth metal hydroxides such as calcium hydroxide, magnesium hydroxide, alkali metal carbonates such as sodium carbonate, potassium carbonate, alkali metal hydrogen carbonates such as sodium hydrogen carbonate, potassium hydrogen carbonate, organic bases such as aniline, diethylamlne, triethylamine, pyridine, and ammonia. Among them, sodium hydroxide is preferably used.

In the present invention, when Pt catalyst is used, amount of the alkaline substance to be used is less than 0.5 m equivalents, preferably less than 0.2 m equivalent, per one mole of the aryloxyethanol represented by the formula (1), wherein m has the same meaning as defined in the formula (1).

If the aryloxyethanol is produced by using a small amount of alkali in its producing process, it may be applied for the reaction of the present invention in which Pt catalyst is used after neutralizing the alkali and also may be used without neutralizing the alkali.

In the reaction of the present invention, the use of alkaline substance is preferable for increasing reaction rate. However, even in the absence of alkali, the reaction can be carried out by using the Pt catalyst.

When using Pt catalyst, the alkali can exist from the beginning of the reaction, and it also can be added in the middle of the reaction. When the alkali is added in the middle of the reaction, the amount of alkali which exists at the beginning is preferably less than 0.1 m equivalents, more preferably 0.05 m equivalents, and the total amount of alkali is less than 0.5 m equivalents per one mole of the aryloxyethanol.

The alkaline substance can be added successively or intermittently.

In both cases of using Pd/In,Cu catalyst and using Pt catalyst, the oxygen-containing gas may be oxygen gas, mixed gas of oxygen and gas inert to the reaction such as nitrogen, argon. To regulate the partial pressure of oxygen, mixed gas of oxygen and nitrogen can be used. Air is preferred because of its low price, and mixed gas of air and nitrogen can be used to regulate the partial pressure of oxygen.

The reaction pressure is generally from about 0.05 MPa to about 10 MPa, preferably from about 0.1 MPa to about 3 MPa.

Although the reaction temperature is not particularly limited, it is usually from about 10° C. to about a boiling temperature under reaction conditions, preferably from about 50° C. to about the boiling temperature under reaction conditions.

The reaction in the present invention may be carried out in either a batch system or a continuous system. A type of a reactor may be any one of a slurry bed, a fixed bed, a fluidized bed, and a trickle-bed.

Progress of the reaction can be traced with a high performance liquid chromatography, gas chromatography, etc. It can also be traced by the measurement of oxygen absorbed.

Thus the target compound, the aryloxyacetic acid represented by the formula (2), can be obtained. When the reaction is carried out in the alkaline aqueous medium, the target compound can be isolated, for example, by separating the catalyst from the reaction mass by filtration or the like, neutralizing or acidifying the filtrate with acid, if necessary, followed by concentration, and then collecting crystals by filtration. Alternatively, the target compound can be isolated by neutralizing or acidifying the filtrate with acid, then extracting the filtrate with a hydrophobic organic solvent, followed by evaporating the solvent from the extract. In the case where the reaction is carried out in the practical absence of an alkali, the target compound can be isolated, for example, by separating the catalyst from the reaction mass by filtration and then concentrating the filtrate. It can also be isolated by extracting the reaction mass with a hydrophobic organic solvent and then evaporating the solvent. The isolated target compound can be further purified through purifying operations such as distillation, recrystallization, extraction and chromatography, as needed.

According to the present invention, when a specific catalyst in which palladium and an indium compound and/or a copper compound are combined is used, elution of the catalyst components into a reaction mass can be suppressed.

Further, the desired aryloxyacetic acid represented by the formula (2) can be produced even in the practical absence of alkali by using a specific catalyst, Pt catalyst. Consequently, amount of alkali required for producing the aryloxyacetic acid can be reduced. Moreover, in the process which is carried out in the presence of alkali, since the aryloxyacetic acid of formula (2) is obtained in the form of an alkali salt, an equivalent amount of acid relative to the alakali is required for neutralization. In contrast, by carrying out the production of the aryloxyacetic acid of formula (2) in the practical absence of alkali, a drastic reduction of the use of acid and an omission of the neutralization step can be achieved.

The present invention will be explained in detail by reference to the following examples, which do not limit the scope of the invention.

EXAMPLE 1

Into a 500 ml round bottomed flask, 2.86 g of 35% hydrochloric acid, 300 g of water and 1.23 g of indium chloride tetrahydrate were added and heated up to 40° C. To this mixture was added 100 g of 5%Pd/activated carbon powder (5% by weight of palladium is supported on activated carbon powder manufactured by N.E. Chemcat Corporation, type R, solid content 47.85%) and the resulting mixture was stirred at that temperature for one hour. 10% aqueous sodium hydroxide solution was subsequently added dropwise over one hour and then a solid component was separated by filtration. By washing the solid component with water until the conductivity of the washing became 0.1 mS/cm, a catalyst comprising palladium and indium was obtained.

Subsequently, into a 500 ml stainless steel reactor equipped with a back pressure regulating valve, a gas meter and a mass flow controller were charged 6.0 g, on a solid basis, of the catalyst obtained above, 20 g of 1,3-bis (hydroxyethoxy)benzene and 18.3 g of a 48% aqueous sodium hydroxide solution, and a reaction was carried out under conditions including a stirring speed of 500 rpm, a reaction pressure of 1.1 MPa and a temperature of 90° C. by passing compressed air at a flow rate of 200 ml/min, which was a converted value under the ordinary temperature and pressure. A gas flow rate from the back pressure regulating valve was measured and the time when oxygen was no longer absorbed was determined to be the completion of the reaction. The oxygen absorption ceased in 5 hours and 10 minutes. After separating the catalyst by filtration, the reaction solution was measured by high performance liquid chromatography (HPLC) to obtain a yield of 1,3-phenyleneoxydiacetic acid. The yield was 96.8%. Elution amounts of palladium and indium in the reaction solution were determined by ICP emission analysis. Elution rates [(amount of eluted metals/amount of metals in catalyst)× 100] were calculated and shown in Table 1.

EXAMPLE 2

Operations were carried out in the same manner as Example 1 except for using 1.3 g of copper chloride dehydrate in place of indium chloride tetrahydrate. The oxygen absorption ceased in 5 hours. The yield of 1,3-phenyleneoxydiacetic acid was 95.1%. Elution rates of metals are shown in Table 1.

EXAMPLE 3

Operations were carried out in the same manner as Example 1 except for using 5%Pd-1%In/C catalyst (manufactured by N.E. Chemcat Corporation. The abbreviation "5%Pd-1%In/C" indicates that components of the catalyst are palladium and indium, contents of the palladium and indium are 5% by weight and 1% by weight, respectively, based on the solid in the catalyst, and carrier is carbon. Hereinafter in this specification, similar abbreviations will be used, in which the before slash indicates component(s) of the catalyst and content(s) based on the solid in the catalyst, and the after slash indicates carrier in the catalyst), which was produced by sequentially supporting palladium and indium on a type K activated carbon, followed by being reduced by hydrogen, in place of the catalyst produced and used in Example 1, and changing the flow rate of compressed air to 600 ml/min from 200 ml/min. The yield of 1,3-phenyleneoxydiacetic acid was 96.9%. Elution rates of metals are shown in Table 1.

EXAMPLE 4

Operations were carried out in the same manner as Example 3 except for using 5%Pd-1%In/C catalyst (manufactured by N.E. Chemcat Corporation), which was produced by coprecipitating palladium and indium to support them on a type K activated carbon at one time, followed by being reduced by hydrogen, in place of the catalyst used in Example 3. The yield of 1,3-phenyleneoxydiacetic acid was 93.2%. Elution rates of metals are shown in Table 1.

EXAMPLE 5

Operations were carried out in the same manner as Example 3 except for using 5%Pd-1%Cu/C catalyst (manufactured by N.E. Chemcat Corporation), which was produced by sequentially supporting palladium and copper on a type K activated carbon, followed by being reduced by hydrogen, in place of the catalyst used in Example 3. The yield of 1,3-phenyleneoxydiacetic acid was 95.8%. Elution rates of metals are shown in Table 1.

EXAMPLE 6

Operations were carried out in the same manner as Example 3 except for using 5%Pd-1%Cu/C catalyst (manufactured by N.E. Chemcat Corporation.), which was produced by coprecipitating palladium and copper to support them on a type K activated carbon at one time, followed by being reduced by hydrogen, in place of the catalyst used in Example 3. The yield of 1,3-phenyleneoxydiacetic acid was 80.7%. Elution rates of metals are shown in Table 1.

COMPARATIVE EXAMPLE 1

Operations were carried out in the same manner as Example 1 except for using 0.08 g of nickel chloride in place of indium chloride tetrahydrate. The oxygen absorption ceased in 5 hours. The yield of 1,3-phenyleneoxydiacetic acid was 91.1%. Elution rates of metals are shown in Table 1.

COMPARATIVE EXAMPLE 2

Operations were carried out in the same manner as Example 1 except for using 6.0 g. on a solid basis, of a commercially available 5% Pd activated carbon powder (manufactured by N.E. Chemcat Corporation) in place of the prepared catalyst used in Example 1. The oxygen absorption ceased in 5 hours 23 minutes. The yield of 1,3-phenyleneoxydiacetic acid was 92.7%. Elution rates of metals are shown in Table 1.

COMPARATIVE EXAMPLE 3

Operations were carried out in the same manner as Example 1 except for using 6.0 g, on a solid basis, of a commercially available 5% Pd-1% Te activated carbon powder (manufactured by N.E. Chemcat Corporation) in place of the prepared catalyst used in Example 1. The oxygen absorption ceased in 4 hours 20 minutes. The yield of 1,3-phenyleneoxydiacetlc acid was 96.5%. Elution rates of metals are shown in Table 1.

COMPARATIVE EXAMPLE 4

Operations were carried out in the same manner as Example 1 except for using 6.0 g, on a solid basis, of a commercially available 5% Pd-2.5% Ag activated carbon powder (manufactured by N.E. Chemcat Corporation) in place of the prepared catalyst used in Example 1 and changing the reaction pressure to 1.3 MPa. The oxygen absorption ceased in 3 hours. Elution rates of metals are shown in Table 1.

TABLE 1

| No. | Catalyst | Elution rate of Palladium | Elution rate of the second component |
|---|---|---|---|
| Example 1 | 5% Pd-1% In/C | <0.1% | <0.5% |
| Example 2 | 5% Pd-1% Cu/C | <0.1% | <0.5% |
| Example 3 | 5% Pd-1% In/C Method A | 0.16% | <0.3% |
| Example 4 | 5% Pd-1% In/C method B | 0.07% | <0.3% |
| Example 5 | 5% Pd-1% Cu/C method A | 0.02% | <0.3% |
| Example 6 | 5% Pd-1% Cu/C method B | 0.02% | <0.3% |
| Comparative example 1 | 5% Pd-1% Ni/C | 0.5% | <0.5% |
| Comparative example 2 | 5% Pd/C | 0.57% | — |
| Comparative example 3 | 5% Pd-1% Te/C | 0.23% | 35% |
| Comparative example 4 | 5% Pd-2.5% Ag/C | 0.47% | <0.5% | method A: the catalyst was produced by sequentially supporting the components on the carrier, followed by being reduced by hydrogen.

method B: the catalyst was produced by coprecipitating the components to support them on the carrier, followed by being reduced by hydrogen.

EXAMPLE 7

Into a 500-ml flask equipped with a cooling condenser, a thermometer, a gas blow tube, a turbine stirring vane and a platelike baffle, 20 g of 1,3-bis(hydroxyethoxy)benzene, 200 g of ion-exchange water and 12 g, on a solid basis, of 5%Pt/C wherein platinum was supported on peat (manufactured by N.E. Chemcat Corporation, type NX, solid content 48%) were charged, and air was blown into the mixture at a rate of 800 ml/min, for 15 hours while stirring at 90° C. and 800 rpm. The analysis of the reaction mass by high performance liquid chromatography revealed that the yield of 1,3-phenylenedioxydiacetic acid was 85.0%.

EXAMPLES 8 TO 13 AND COMPARATIVE EXAMPLES 5 TO 9

Operations were carried out in the same manner as Example 7 except for using a catalyst shown below in place of the catalyst used in Example 7. The results are shown in Table 2.

Catalyst Used in Each Example

EXAMPLE 8

5%Pt/C, wherein platinum was supported on charcoal (manufactured by N.E. Chemcat Corporation, type AC, solid content 48%).

EXAMPLE 9

5%Pt/titania, wherein platinum was supported on titania (manufactured by N.E. Chemoat Corporation, solid content 48%).

EXAMPLE 10

5%Pt-2%Bi/C, wherein platinum and bismuth were supported on charcoal (manufactured by N.E. Chemcat Corporation, type K, solid content 48%).

EXAMPLE 11

5%Pt-5%Bi/C, wherein platinum and bismuth were supported on charcoal (manufactured by N.E. Chemcat Corporation, type K, solid content 48%).

EXAMPLE 12

5%Pt-1%Te/C, wherein platinum and tellurium were supported on charcoal (manufactured by N.E. Chemcat Corporation, type K, solid content 48%).

EXAMPLE 13

5%Pt-2%Pb/C, wherein platinum and lead were supported on charcoal (manufactured by N.E. Chemcat Corporation, type K, solid content 48%).

COMPARATIVE EXAMPLE 5

5%Pd/C, wherein palladium was supported on peat (manufactured by N.E. Chemcat Corporation, type NX, solid content 48%).

COMPARATIVE EXAMPLE 6

5%Pd/C, wherein palladium was supported on charcoal (manufactured by N.E. Chemcat Corporation, type K, solid content 48%).

COMPARATIVE EXAMPLE 7

5%Rh/C, wherein rhodium was supported on peat (manufactured by N.E. Chemcat Corporation. type NX, solid content 48%).

COMPARATIVE EXAMPLE 8

5%Ru/C, wherein ruthenium was supported on peat (manufactured by N.E. Chemcat Corporation, type NX, solid content 48%).

COMPARATIVE EXAMPLE 9

5%Pd-1%Te/C, wherein palladium and tellurium were supported on peat (manufactured by N.E. Chemcat Corporation, type NX, solid content 48%).

EXAMPLES 14 TO 16

Operations were carried out in the same manner as Example 7 except for using a catalyst shown below in place of the catalyst used in Example 7, and changing amount of the catalyst to 6.0 g from 12.0 g. The results are shown in Table 2.

Catalyst Used in Each Example

EXAMPLE 14

5%Pt-2%Bi-10%W/C, wherein platinum, bismuth and tungsten were supported on charcoalt (manufactured by N.E. Chemcat Corporation, type K, solid content

EXAMPLE 15

5%Pt-2%Bi-10%Mo/C, wherein platinum, bismuth and molybdenum were supported on charcoalt (manufactured by N.E. Chemcat Corporation, type K, solid content 48%).

EXAMPLE 16

5%Pt-2%Bi-10%Sn/C, wherein platinum, bismuth and tin were supported on charcoalt (manufactured by N.E. Chemcat Corporation, type X, solid content 48%).

TABLE 2

| No. | Catalyst | Catalyst weight (g) | Yield (%) |
| --- | --- | --- | --- |
| Example 7 | 5% Pt/C(NX) | 12 | 85.0 |
| Example 8 | 5% Pt/C(AC) | 12 | 69.3 |
| Example 9 | 5% Pt/titania | 12 | 32.8 |
| Example 10 | 5% Pt-2% Bi/C(K) | 12 | 82.7 |
| Example 11 | 5% Pt-5% Bi/C(K) | 12 | 85.5 |
| Example 12 | 5% Pt-1% Te/C(K) | 12 | 31.9 |
| Example 13 | 5% Pt-1% Pb/C(K) | 12 | 31.2 |
| Example 14 | 5% Pt-2% Bi-10% W/C(K) | 6 | 78.5 |
| Example 15 | 5% Pt-2% Bi-10% Mo/C(K) | 6 | 72.1 |
| Example 16 | 5% Pt-2% Bi-10% Sn/C(K) | 6 | 71.9 |
| Comparative example 5 | 5% Pd/C(NX) | 12 | 1.5 |
| Comparative example 6 | 5% Pd/C(K) | 12 | 0.7 |
| Comparative example 7 | 5% Rh/C(NX) | 12 | 0.3 |
| Comparative example 8 | 5% Ru/C(NX) | 12 | 0.6 |
| Comparative example 9 | 5% Pd-1% Te/C(NX) | 12 | 2.4 |

EXAMPLE 17

Into a 500-ml flask equipped with a cooling condenser, a thermometer, a gas blow tube, a turbine stirring vane and a platelike baffle, 20 g of 1,3-bis(hydroxyethoxy)benzene, 200 g of ion-exchange water, 0.4 g of sodium hydroxide, and 12 g, on a solid basis, of 5%Pt/C wherein platinum was supported on peat (manufactured by N.E. Chemcat Corporation, type NX, solid content 48%) were charged, and air was blown into the mixture at a rate of 800 ml/min, for 15 hours while stirring at 90° C. and 800 rpm. The analysis of the reaction mass by high performance liquid chromatography revealed that the yield of 1,3-phenylenedioxydiacetic acid was 82.4%.

EXAMPLE 18

Operations were carried out in the same manner as Example 17, except for changing the amount of sodium hydroxide to 1.29 from 0.4 g. The results are shown in Table 3.

EXAMPLE 19

Operations were carried out in the same manner as Example 17 except for using 5%Pt-2%Bi/C wherein platinum and bismuth were supported on charcoal (manufactured by N.E. Chemcat Corporation, type K, solid content 48%)in place of the catalyst used in Example 17. The results are shown in Table 3.

EXAMPLE 20

Operations were carried out in the same manner as Example 19, except for changing the amount of sodium hydroxide to 1.2 g from 0.4 g. The results are shown in Table 3.

COMPARATIVE EXAMPLE 10

Operations were carried out in the same manner as Example 17, except for changing the amount of sodium hydroxide to 9.1 g from 0.4 g. The results are shown in Table 3.

TABLE 3

| No. | Catalyst | NaOH weight (g) | Yield (%) |
|---|---|---|---|
| Example 17 | 5% Pt/C(NX) | 0.4 | 82.4 |
| Example 18 | 5% Pt/C(NX) | 1.2 | 78.6 |
| Example 19 | 5% Pt-2% Bi/C(K) | 0.4 | 84.0 |
| Example 20 | 5% Pt-2% Bi/C(NX) | 1.2 | 83.0 |
| Comparative example 10 | 5% Pt/C(NX) | 9.1 | 23.1 |

EXAMPLE 21

Into a 500-ml flask equipped with a cooling condenser, a thermometer, a gas blow tube, a turbine stirring vane and a platelike baffle, 20 g of 1,3-bis(hydroxyethoxy)benzene, 200 g of ion-exchange water, and 6 g. on a solid basis, of 5% Pt/C wherein platinum was supported on peat (manufactured by N.E. Chemcat Corporation, type K, solid content 48%) were charged, and air was blown into the mixture at a rate of 800 ml/min, for 15 hours while successively dosing 44 g of 10% sodium hydroxide aqueous solution and stirring at 95° C. and 800 rpm. The analysis of the reaction mass by high performance liquid chromatography revealed that the yield of 1,3-phenylenedioxydiacetic acid was 88.2%.

What is claimed is:

1. A process for producing an aryloxyacetic acid represented by the formula (2):

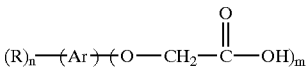

wherein m represents an integer of 1 or 2, n represents an integer from 0 to 4, Ar represents an aromatic hydrocarbon ring;

each R independently represents an alkyl group, a cycloalkyl group, an aryl group, an alkoxy group, a cycloalkoxy group, an aryloxy group, a halogen atom, an alkylcarbonyl group, an arylcarbonyl group, a carboxyl group or a nitro group, comprising a step of reacting an oxygen-containing gas with an aryloxyethanol represented by the formula (1):

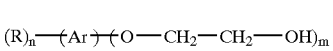

wherein m, n, Ar, and R, respectively, have the same meanings as defined above;

in the presence of a catalyst comprising
palladium and at least one of an indium compound and a copper compound in an aqueous medium and in the presence of 0.5 m or more equivalent of alkali per one mole of the aryloxyethanol represented by the formula (1); or
in the presence of a platinum catalyst, in an aqueous medium and in the absence of alkali or in the presence of less than 0.5 m equivalent of alkali per one mole of the aryloxyethanol represented by formula (1).

2. The process according to claim 1 wherein the step of reacting an oxygen-containing gas with the aryloxyethanol of formula (1) in the presence of a platinum catalyst, in an aqueous medium and in the absence of alkali or in the presence of less than 0.5 m equivalent of alkali per one mole of the aryloxyethanol represented by the formula (1).

3. The process according to claim 2 wherein the amount of alkali which exists at the beginning is less than 0.1 m equivalent per one mole of the aryloxyethanol represented by the formula (1) and the alkali is added in the middle of the reaction.

4. The process according to claim 2 wherein the platinum catalyst is supported on a carrier.

5. The process according to claim 4 wherein the component of platinum catalyst is platinum.

6. The process according to claim 5 wherein the components of platinum catalyst are platinum and bismuth.

7. The process according to claim 6 wherein the components of platinum catalyst are platinum, bismuth, and one or more other metals selected from chromium, molybdenum, tungsten, vanadium, niobium, tantalum, germanium, tin, and lead.

8. The process according to claim 4 wherein the carrier is an activated carbon.

9. The process according to claim 2 wherein the aqueous medium is water or a mixed solvent consisting of water and a lower carboxylic acid.

10. The process according to claim 1 wherein the aryloxyethanol is bis(hydroxyethoxy)benzene.

11. A process for producing an aryloxyacetic acid represented by the formula (2):

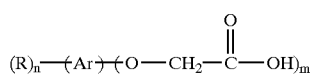 (2)

wherein m represents an integer of 1 or 2, n represents an integer from 0 to 4,

Ar represents an aromatic hydrocarbon ring,

R independently represents an alkyl group, a cycloalkyl group, an aryl group, an alkoxy group, a cycloalkoxy group, an aryloxy group, a halogen atom, an alkylcarbonyl group, an arylcarbonyl group, a carboxyl group or a nitro group, comprising a step of reacting an oxygen-containing gas with an aryloxyethanol represented by the formula (1):

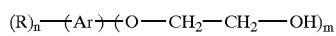 (1)

wherein, m, n, Ar, and R, respectively, have the same meanings as defined above, in the presence of a catalyst comprising
palladium and at least one of an indium compound and a copper compound in an aqueous medium and
in the presence of 0.5 m equivalent or more of alkali per one mole of the aryloxyethanol represented by the formula (1).

12. The process according to claim 1 or 11 wherein the catalyst is supported on a carrier.

13. The process according to claim 12 or 11 wherein the carrier is an activated carbon.

14. The process according to claim 1 or 11 wherein the aqueous medium is water.

15. The process according to claim 11, wherein the aqueous medium is water.

16. A process for producing an aryloxyacetic acid represented by the formula (2):

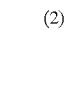 (2)

wherein m represents an integer of 1 or 2, n represents an integer from 0 to 4,

Ar represents an aromatic hydrocarbon ring,

R independently represents an alkyl group, a cycloalkyl group, an aryl group, an alkoxy group, a cycloalkoxy group, an aryloxy group, a halogen atom, an alkylcarbonyl group, an arylcarbonyl group, a carboxyl group or a nitro group, comprising a step of reacting an oxygen-containing gas with an aryloxyethanol represented by the formula (1):

 (1)

wherein m, n, Ar, and R, respectively, have the same meanings defined above, in the presence of a catalyst consisting essentially of platinum in an aqueous medium and in the absence of alkali or in the presence of less than 0.5 m equivalent of alkali per one mole of the aryloxyethanol represented by the formula (1).

17. A process according to claim 16, wherein the catalyst is supported on a carrier.

18. The process according to claim 17, wherein the carrier is an activated carbon.

* * * * *